(12) United States Patent
Neidle et al.

(10) Patent No.: US 6,589,971 B1
(45) Date of Patent: Jul. 8, 2003

(54) BIS-BENZAZOLES AND THEIR USE AS ANTINEOPLASTIC AGENTS

(75) Inventors: Stephen Neidle, Herts (GB); John Monn, Belfast (GB)

(73) Assignees: The Queens University of Belfast, Belfast (IR); Institute of Cancer Research, London (GB); The University of Reading, Reading (GB)

( * ) Notice: Subject to any disclaimer, the term of this patent is extended or adjusted under 35 U.S.C. 154(b) by 0 days.

(21) Appl. No.: 09/959,084

(22) PCT Filed: Apr. 17, 2000

(86) PCT No.: PCT/GB00/01479

§ 371 (c)(1),
(2), (4) Date: Apr. 18, 2002

(87) PCT Pub. No.: WO00/63180

PCT Pub. Date: Oct. 26, 2000

(30) Foreign Application Priority Data

Apr. 16, 1999 (GB) .............................................. 9908828

(51) Int. Cl.⁷ .................. A61K 31/4184; C07D 403/04
(52) U.S. Cl. ..................................... 514/394; 548/305.4
(58) Field of Search ........................ 548/305.4; 514/394

(56) References Cited

U.S. PATENT DOCUMENTS 5,824,698 A * 10/1998 Hasler et al. ............... 514/394

FOREIGN PATENT DOCUMENTS

| EP | 0 653 491 | 5/1995 |
|---|---|---|
| WO | WO 96 06831 | 3/1996 |
| WO | WO 96/16042 | 5/1996 |

OTHER PUBLICATIONS

Conley et al., CA 78:16594, 1973.*
CA Registry No. 47864–06–2., 1974.*
CA Registry No. 103319–65–9, 1986.*
Connell et al., CA 123:170505, 1995.*
E.V. Bichenkova et al. "Strong, specific reversible binding ligands for transfer RNA: Comparison by fluorescense and NMR spectroscopies with distamycin binding for a new structural claa of ligand", *Nucleostides Nucleotides*, vol. 17, No. 9–11, 1998, pp. 1651–1665.
S. Neidle et al., "Symmetric bis–benzimidazoles: New sequence–selective DNA–binding molecules", *Chemical Communications*, No. 10, May 21, 1999, pp. 929–930.

* cited by examiner

Primary Examiner—Laura L. Stockton
(74) Attorney, Agent, or Firm—Dann, Dorfman, Herrell & Skillman, P.C.

(57) ABSTRACT

"Head-to-head" bis-benzimidazoles having the following formula

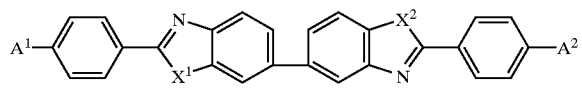

wherein $A^1$, $A^2$, $X^1$ and $X^2$ are as defined in the following specification, have been found to bind to specific sequences in the minor groove of duplex DNA, and to have cytotoxic effects against a range of tumor cell lines.

12 Claims, 1 Drawing Sheet

BIS-BENZAZOLES AND THEIR USE AS ANTINEOPLASTIC AGENTS

This application is a 371 of PCT/GB00/01479 filed Apr. 17, 2000.

TECHNICAL FIELD

The present invention relates to bis-benzimidazoles and related compounds, many of which are novel; to uses and compositions of such compounds; and to methods for their preparation.

BACKGROUND ART

The minor groove of duplex DNA is the site of non-covalent interaction of a large number of anticancer drugs, antibiotics and antiviral agents, which are believed to exert their action by competing with transcription factors or architectural proteins, such as E2F, TATA-box binding proteins or DNA topoisomerase I/II. The molecular basis of DNA recognition for a number of drugs in this super-family (notably distamycin, netropsin, berenil, pentamidine and Hoechst 33258) has been extensively studied, notably by crystallography, NMR and footprinting methods. These studies have shown that their AT preferences are a consequence of, in particular, (i) the sequence-dependent narrow width of the minor groove of B-form DNA, resulting in stabilisation by van der Waals interactions with the walls of the groove, and (ii) their ability to form specific hydrogen bonds with donor and acceptor atoms on the minor-groove edge of A:T base pairs. These factors have been utilised in the design of molecules with altered and extended recognition properties, some of which are capable of sequence-specific gene regulation. Hoechst 33258 is a bis-benzimidazole derivative (I):

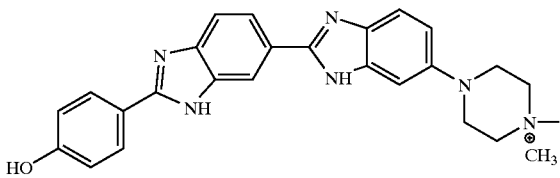

The benzene ring of one benzimidazole system is linked to the imidazole ring of the other. Such structures may be termed "head to tail".

Crystallographic analyses of a number of oligonucleotide complexes with Hoechst 33258, and several of its derivatives, including a tris-benzimidazole with an extended recognition site, have shown that each benzimidazole sub-unit interacts with two A:T base pairs by means of a pair of cross-strand hydrogen bonds. The head-to-tail arrangement forces the site for each successive subunit to overlap the previous one by one base-pair, so that each benzimidazole group in Hoechst 33258 and other head-to-tail analogues effectively recognises 1.5 A:T base pairs.

(N Spink, D G Brown, J V Skelly and S Neidle, *Nucleic Acids Res.*, 1994, 22, 1607; G R Clark, D W Boykin, A Czarny and S Neidle, *Nucleic Acids Res.*, 1997, 25, 1510; G R Clark, E J Gray, S Neidle, Y-H Li and W Leupin, *Biochemistry*, 1996, 35, 13745).

A symmetrical head-to-head benzimidazole has recently been reported (E V Bichenkova et al, *Nucleosides and Nucleotides*, 1998, 17, 1651). This is 2,2'-bis(4-hydroxyphenyl)-6,6'-bis-benzimidazole. It was prepared by the reaction of 3,3'-diaminobenzidine with ethyl 4-hydrozybenzimidate hydrochloride in boiling acetic acid. It is reported that this compound binds specifically to t-RNA, as do Hoechst 33258 and distamycin.

DISCLOSURE OF INVENTION

Molecular modelling, based on these structural studies, suggested to us that compounds with a symmetric head-to-head benzimidazole arrangement, and other analogues, could also bind in the minor groove in an effective manner. This arrangement would extend the size of the bis-benzimidazole recognition site from three (in Hoechst 33258 and analogues) to four consecutive A:T base pairs, with distinctive cross-strand hydrogen bonding involving each base pair. This arrangement thus extends the effective recognition of each benzimidazole sub-unit to two A:T base pairs. The modelling used the structures of the self-complementary duplex sequences d(CGCGAATTCGCG) and d(CGCAAATTTGCG), as found in several relevant drug complexes. It suggested that the central 5'-AATT sequence would be an optimal site for the head-to-head motif and for maintenance of helical register with all four consecutive base pairs without necessitating significant DNA conformational change. We have also appreciated that the motif could provide a platform for adding further functionality which could specifically recognise bases beyond the central core of four A:T base pairs.

In a first aspect the present invention provides a compound of the formula II (and tautomers):

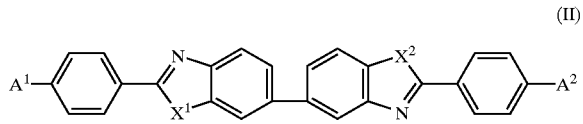

where $X^1$ and $X^2$ are each independently selected from NH, O and S ($X^1$ and $X^2$ preferably being the same) and $A^1$ and $A^2$ are independently selected from: —Y—Q—Z where Y is selected from O, NH and S; Q is selected from —(CH$_2$)$_n$— where n is 0–10 and carbocyclic 3–7 membered rings; and Z is selected from H, NR$^3$R$^4$ (where each of R$^3$ and R$^4$ is selected from H; a saturated or unsaturated carbon chain of up to 10 carbon atoms or a ring of up to 7 carbon atoms), or a heterocyclic ring preferably of 3–8 atoms with 1–3 heteroatoms selected from O, S and N; and —LM where M is an alkylating agent functionality, particularly a nitrogen mustard functionality e.g. —N(CH$_2$CH$_2$Cl)$_2$, preferably Aryl-N(CH$_2$CH$_2$Cl)$_2$, and L is a linking group e.g.

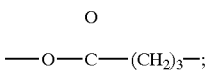

wherein $A^1$ and $A^2$ are preferably the same; or a pharmaceutically acceptable salt thereof; with the proviso that if $X^1=X^2=$NH, then $A^1$ and $A^2$ are not both OH.

In a second aspect the invention provides a pharmaceutical composition comprising a compound of the formula II where $X^1$ and $X^2$ are each independently selected from NH, O and S ($X^1$ and $X^2$ preferably being the same) and $A^1$ and $A^2$ are independently selected from: —Y—Q—Z where Y is selected from O, NH and S; Q is selected from —(CH$_2$)$_n$— where n is 0–10 and carbocyclic 3–7 membered rings; and Z is selected from H, NR$^3$R$^4$ (where each of R$^3$ and R$^4$ is selected from H; a saturated or unsaturated carbon chain of up to 10 carbon atoms or a ring of up to 7 carbon atoms), or a heterocyclic ring preferably of 3–8 atoms with 1–3 heteroatoms selected from O, S and N; and —LM where M is an alkylating agent functionality, particularly a nitrogen mustard functionality e.g. —N(CH$_2$CH$_2$Cl)$_2$, preferably Aryl-N(CH$_2$CH$_2$Cl)$_2$, and L is a linking group e.g.

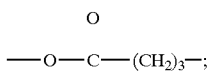

wherein A$^1$ and A$^2$ are preferably the same; or a pharmaceutically acceptable salt thereof.

In a third aspect the invention provides the use of a compound of formula (II) as defined in the second aspect in the manufacture of a composition for therapeutic use as a cytotoxic, antibiotic or antiviral agent.

A fourth aspect of the present invention is the use of a compound as described in the first aspect of the invention, disregarding the proviso, in a method of therapy. Conditions which may be treated include gene-based diseases, including, for example, neoplastic diseases, and also bacterial, parasitic and viral infections. Any condition which may be treated by the regulation of gene expression may be treated using compounds of the invention. In accordance with this aspect of the present invention, the compounds provided may be administered to individuals. Administration is preferably in a "therapeutically effective amount", this being sufficient to show benefit to a patient. Such benefit may be at least amelioration of at least one symptom. The actual amount administered, and rate and time-course of administration, will depend on the nature and severity of what is being treated. Prescription of treatment, e.g. decisions on dosage, is within the responsibility of general practitioners and other medical doctors.

A compound may be administered alone or in combination with other treatments, either simultaneously or sequentially dependent upon the condition to be treated.

Pharmaceutical compositions according to the present invention, and for use in accordance with the present invention, may comprise, in addition to the active ingredient, i.e. a compound of formula II, a pharmaceutically acceptable excipient, carrier, buffer, stabiliser or other materials well known to those skilled in the art. Such materials should be non-toxic and should not interfere with the efficacy of the active ingredient. The precise nature of the carrier or other material will depend on the route of administration, which may be oral, or by injection, e.g. cutaneous, subcutaneous, or intravenous.

Pharmaceutical compositions for oral administration may be in tablet, capsule, powder or liquid form. A tablet may comprise a solid carrier or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included. A capsule may comprise a solid carrier such a gelatin.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

Preferred compounds of the invention are symmetrical: that is both X$^1$=X$^2$ and A$^1$=A$^2$.

In a further aspect the invention provides a method of preparing a symmetrical compound of formula (II) by condensing a biphenyl compound of formula (III)

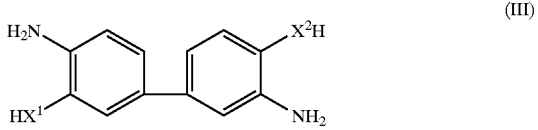

with a benzaldehyde of formula (IV)

Thus a preferred synthetic route to symmetrical bis-benzimidazoles (V) is as shown in the accompanying FIG. 1.

MODES FOR CARRYING OUT THE INVENTION

Figure 1:
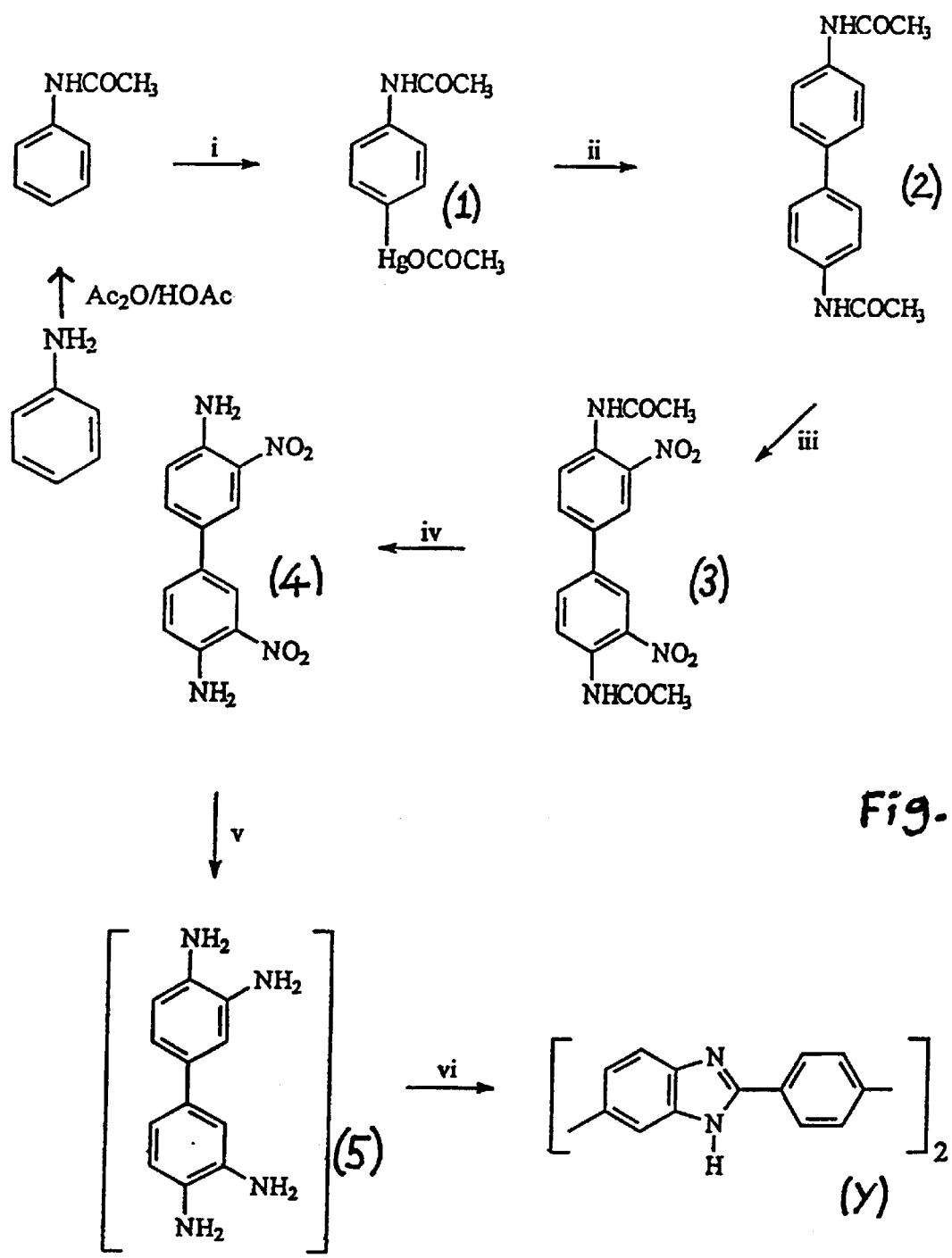
FIG. 1 is a synthetic scheme for symmetrical bis-benzimidazoles.

The invention will now be illustrated by means of some examples.

A) Synthesis

Head-to-head benzimidazoles of formula (7) can be synthesised from 3,3',4,4'-tetraaminobiphenyl (5). This is commercially available. We preferred to synthesise it from aniline (see FIG. 1). The compound (5) is condensed with a 4-substituted benzaldehyde (6) by heating in an inert solvent, e.g. nitrobenzene.

Aniline was N-acetylated. The acetanilide was then 4-mercurated using mercuric acetate and perchloric acid in acetic acid at room temperature. The resulting arylmercuric compound (1) was dimerised by treatment with copper and a catalytic amount of PdCl$_2$ in pyridine. The product (2) was dinitrated to produce the 3,3' dinitro compound (3). This was deprotected to produce 4,4'-diamino-3,3' dinitrobiphenyl (4). This is a more stable compound than the tetraamino compound (5) and was therefore stockpiled as a raw material.

Synthesis of the 2,2-bis-(4'-Methoxyphenyl)-5,5-bi-1H-benzimidazole (8)

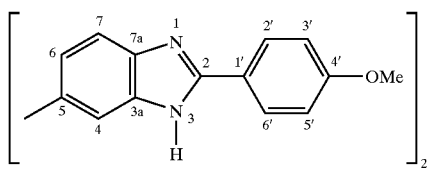

4,4'-Diamino-3,3'-dinitrobiphenyl (2 g, 7.3 mmol) in acetone (70 ml) was reduced by hydrogenation using 40 psi of H$_2$ and a catalytic amount of Raney Nickel for 2 hours. After filtration the solvent was removed in vacuo to obtain a brown solid which was used in the next step without further purification.

This solid and para-anisaldehyde (1.8 ml, 14.6 mmol) in nitrobenzene (20 ml) were heated at 150° C. under argon for 8 hours. To the cooled mixture was added an excess of hexane to afford a precipitate and this was removed by filtration. The precipitate was then purified by column chromatography on silica gel (gradient from 100% of ethyl acetate to 20% acetone\ethyl acetate (v/v)). Concentration in vacuo yielded a pale yellow solid which was redissolved in acetone (1 ml) and precipitated in an excess of hexane (40 ml). Filtration gave the benzimidazole 8 in 29% yield.

m.p.: 267–270° C. $\delta_H$ (400 MHz, DMSO): 3.85 (6H, s, OMe), 7.13 (4H, d, J=8.0 Hz, 3',5'-H), 7.50–7.90 (6H, m, 4,6,7-H), 8.15 (4H, d, J=8.0 Hz, 2',6'-H), 12.82 (2H, s, 3-H). $\delta_c$ (100 MHz, DMSO): 55.3 (OMe), 114.3 (3',5'-C), 116.5 (4-C), 118.6 (7-C), 122.7 (6-C), 127.9 (2',6'-C), 135.2–135.7 (3a, 7a-C), 143.2 (1'-C), 144.6 (5-C), 151.9 (4'-C), 160.6 (2-C). m/z (CI): accurate mass obtained: 447.1827 (MH+); accurate mass required: 447.1820 (MH+);

in acetone (1.5 ml) and an excess of hexane (35 ml) was added to yield a pale yellow precipitate. Filtration afforded 9 in 23% yield.

m.p.: 256–260° C. $\delta_H$ (250 MHz DMSO): 6.93 (4H, d, J=8.6 Hz, 2',6'-H), 7.48–7.88 (6H, m, 4,6,7-H), 8.03 (4H, d, J=8.6 Hz, 3',5'-H), 9.97 (2H, s, OH), 12.71 (2H, s, 3-H); $\delta_c$ (100 MHz DMSO): 115.5 (2',6'-C), 116.3 (4-C), 118.4 (7-C), 121.1 (6-C), 128.1 (3',5'-C), 135.0–135.7 (3a, 7a-C), 143.1 (4'-C), 144.6 (5-C), 152.7 (1'-C), 159.1 (2-C). m/z (CI): accurate mass obtained: 419.1510 (MH+); accurate mass required: 419.1507 (MH+);

Synthesis of the 2,2-bis-[4'-[4"-[para-[bis-(Chloroethyl)-amino]phenyl-]-butyryloxy]-phenyl]-5,5-bi-1H-benzimidazole (10)

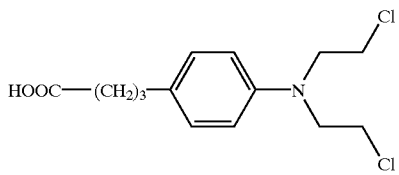

(11)

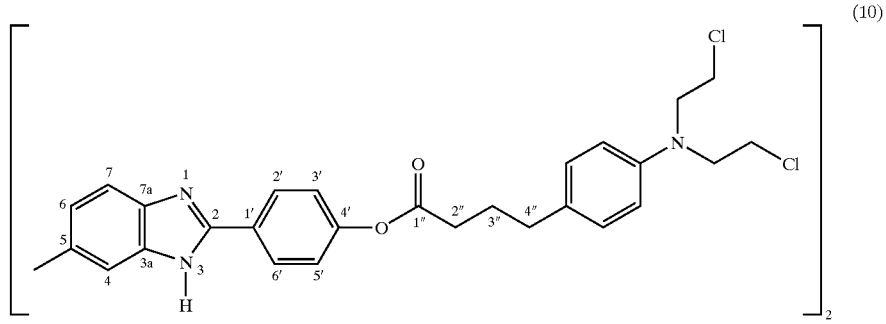

(10)

Synthesis of the 4',4'-[5,5-bi-1H-Benzimidazole]-2,2-diylbis-phenol (9)

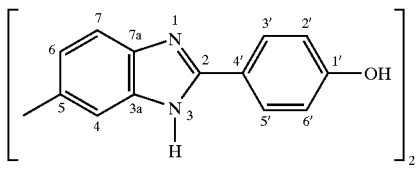

4,4'-Diamino-3,3'-dinitrobiphenyl (500 mg, 1.82 mmol) in acetone (20 ml) was reduced by hydrogenation using 40 psi of $H_2$ and a catalytic amount of Raney Nickel for 2 hours. After filtration the solvent was removed in vacuo to obtain a brown solid which was used in the next step without further purification.

This solid and para-hydroxybenzaldehyde (445 mg, 3.64 mmol) were heated in nitrobenzene (5 ml) at 150° C. under argon for 12 hours. To the cooled mixture was added an excess of hexane (50 ml) to afford a precipitate and this was removed by filtration. The precipitate was then purified by column chromatography on silica gel (gradient from 100% ethylacetate to 10% methanol/ethylacetate (v/v)). Concentration in vacuo afforded a solid. The solid was redissolved Oxalylchloride (50 µl, 0.58 mmol) was added dropwise under argon to DMF (4 ml) at –20° C. to afford a white precipitate. To this slurry was added a solution of chlorambucil (11) (73 mg, 0.24 mmol) in DMF (0.5 ml) and the mixture was warmed to room temperature. The solution was cooled to –20° C. after 2 hours and a solution of 9 (50 mg, 0.12 mmol) in pyridine (0.5 ml) was added. The yellow solution obtained was warmed to room temperature and stirred for 48 hours. An excess of water. (15 ml) was added to yield a precipitate which was filtered and then purified by column chromatography on silica gel (gradient from 1/1 to 8/2 ethylacetate/petroleum ether (v/v)). Concentration in vacuo afforded an oil. This oil was dissolved in acetone (1 ml) and an excess of hexane (40 ml) was added to afford a pale yellow precipitate. Filtration gave 10 in 30% yield.

m.p.: 111–114° C. $\delta_H$ (250 MHz, DMSO): 1.9 (4H, q, J=7.1 Hz, 3"-H), 2.53–2.67 (8H, m, 2",4"-H), 3.71 (16H, s, $NCH_2$—$CH_2Cl$), 6.70 (4H, d, J=7.7 Hz, 4 arom. H), 7.08 (4H, d, J=7.7 Hz, 4 arom. H), 7.33 (4H, d, J=8.3 Hz, 3',5'-H), 7.49–8.02 (6H, m, 4,6,7-H), 8.23 (4H, d, J=8.3 Hz, 2',6'-H), 12.77 (2H, s, 3-H). m/z (FAB): accurate mass obtained: 989.2882 (MH+); accurate mass required: 989.2872 (MH+);

Synthesis of the 5-(3',3'-Dimethylamino-1'-propyloxy)benzaldehyde (12)

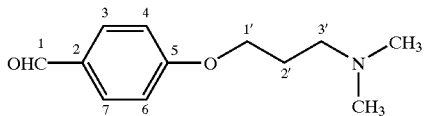

To a solution of p-hydroxybenzaldehyde (5 g, 40.94 mmol), 3-dimethylaminopropan-1-ol (7.27 ml, 61.4 mmol) and triphenyiphosphine (16.1 g, 61.4 mmol) in THF (100 ml) was added at 0° C. under argon diethylazodicarboxylate (9.55 ml, 61.4 mmol). The mixture was warmed slowly to room temperature and stirred for 3 hours. The solvent was removed in vacuo and the dark orange oil obtained purified by column chromatography on silica gel (gradient from 100% DCM to 20% methanol/DCM (v/v)) to give 7.17 g of 12 as a pale yellow oil in 85% yield.

$\delta_H$ (400 CDCl$_3$): 1.99 (2H, tt, J=6.4 Hz, J=7.1 Hz, 2'-H), 2.26 (6H, s, 2 NMe), 2.46 (2H, t, J=7.1 Hz, 3'-H), 4.10 (2H, t, J=6.4 Hz, 1'-H), 7.00 (2H, t, J=8.8 Hz, 4,6H), 7.82 (2H, d, J=8.8 Hz, 3,7-H), 9.88 (1H, s, 1-H). $\delta_c$ (100 MHz, CDCl$_3$): 27.50 (2'-C), 45.52 (2 NMe), 56.14 (3'-C), 66.58 (1'-C), 115.10 (4,6-C), 129.81 (2-C), 132.26 (3,7-C), 164.35 (5-C), 190.83 (1-C). m/z (CI): accurate mass obtained: 208.1337 (MH+); accurate mass required: 208.1337 (MH+);

Synthesis of the 2,2-bis-[4'-(3"-Dimethylamino-1"-propyloxy)phenyl]-5,5-bi-1H-benzimidazole (13)

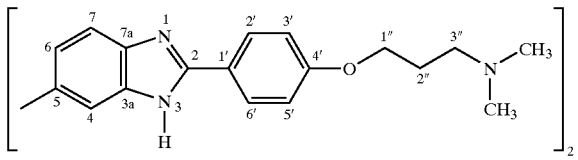

4,4'-Diamino-3,3'-dinitrobiphenyl (1.5 g, 5.47 mmol) in acetone (100 ml) was reduced by hydrogenation using 40 psi of H$_2$ and a catalytic amount of Raney nickel for 3 hours. After filtration the solvent was removed in vacuo to obtain a brown solid which was used in the next step without further purification.

This solid and 5-(3',3'-dimethylamino-1'-propyloxy) benzaldehyde (12) (2.27 g, 10.93 mmol) in nitrobenzene (15 ml) were heated at 150° C. under argon for 12 hours. The mixture was cooled to room temperature and methanol (100 ml) was added. The solution obtained was extracted with hexane (3×100 ml) and the methanol extract concentrated in vacuo to give a brown solid. The solid was then purified by column chromatography on silica gel (hexane and a gradient from 50% ethyl acetate/methanol to 4% Et$_3$N/methanol (v/v)). Concentration in vacuo afforded a solid. The solid was redissolved in acetone (40 ml) and an excess of hexane (400 ml) was added to yield a pale yellow precipitate. Filtration gave 13 in 35% yield.

mp.: 218–220° C. $\delta_H$ (400 MHz DMSO): 1.85–1.88 (4H, m, 2"-H), 2.14 (12H, s, 4 NMe), 2.35 (4H, t, J=6.9 Hz, 3"-H), 4.07 (4H, t, J=6.2 Hz, 1"-H), 7.10 (4H, d, J=8.8 Hz, 3',5'-H), 7.49–7.88 (6H, m, 4,6,7-H), 8.12 (4H, d, J=8.8 Hz, 2',6'-H), 12.80 (2H, s, 3-H). $\delta_c$ (100 MHz DMSO): 27.7 (2"-C), 46.1 (NMe), 56.5 (3"-C), 66.9 (1"-C), 115.7 (3',5'-C), 119.6–119.8 (4,6-C), 122.2 (7-C), 123.4 (5-C), 128.9 (2'-6'-C), 135.8–136.1 (3a, 7a-C), 143.3 (1'-C), 152.0 (4'-C), 160.9 (2-C). m/z (CI): accurate mass obtained: 588.3203 (M+); accurate mass required: 588.3210 (M+).

Crystallographic Analsis of DNA Complexes

Crystallographic analyses have been undertaken on (i) the bis-(hydroxyphenyl) compound (9) co-crystallised with the oligonucleotide sequence (CGCGAATTCGCG), and (ii) its dimethylamino derivative (13) co-crystallised with the sequence d(CGCAAATTTGCG).

Compound (9) was co-crystallised with d(CGCGAATTCGCG) (from Oswell DNA Service, Southampton) using the hanging-drop method at 286 K. Elongated prismatic crystals were obtained from a 1.5 mM solution of compound (9) in 50% w/w MPD, in a droplet containing 10 mM MgCl$_2$ 600 mM KCl, 0.75 mM DNA and 6 mM spermine, equilibrated against 30% w/w MPD. The crystals are orthorhombic, space group P2$_1$2$_1$2$_1$, with cell dimensions a=25.46(2), b=39.96(4) and c=65.66(7) Å.

Intensity data were collected from a flash-frozen crystal maintained at 100 K with a RAXIS-4 image plate detector, using Cu—K$_\alpha$ radiation from a rotating-anode generator and mirror-focussing optics. A total of 6380 unique reflections were obtained after merging Friedel equivalents (R$_{merge}$= 0.044) to a resolution of 1.8 Å. The structure was solved using molecular replacement, and refined with the SHELX-97 package. The final model included 174 water molecules, and had an R of 0.229 for 1657 reflections with F>4σ(F), and 23.2% for all data to 1.8 Å R$_{free}$ was 25.1%.

Compound (13) was treated similarly.

Both crystal structures show a B-form DNA double helix with ligand bound in the A/T region of the minor groove. Both structures show hydrogen bonding between all four central A:T base pairs and the benzimidazole subunits, in full accord with the modelling predictions. Each inner-facing ring nitrogen atom of a benzimidazole ring hydrogen bonds to a thymine O2 atom of one base pair and an adenine N3 atom on the opposite strand of an adjacent one. It is notable that the absence of formal cationic charge in compound (9) does not affect its sequence selectivity, as observed in these two crystal structures (see also below), suggesting that the role of charge is to modulate affinity rather than to determine sequence selectivity.

DNase I Footprinting

These preferences have also been observed in DNase I footprinting studies with a natural DNA fragment, which have shown that compounds (9) and (13) both interact preferentially with some A/T sites. Compound (13) binds to AT-sites between 7–10 fold better than compound (9) and has an especially high affinity for the 5'-AATT site (30 nm). Quantitative footprinting data indicated that the order of preference is 5'-AATT>5'-ATAT>5'-TAAT>5'-TATA~5'-TTAA, similar to that previous determined for Hoechst 33258. It is notable that the increased affinity of compound (13) relative to compound (9) does not affect its sequence selectivity. This enhanced binding strength may be a consequence of its cationic charge or its increased DNA site size, since the crystal structure of the complex with D(CGCAAATTTGCG)$_2$ shows it to cover six base pairs. The ability of the head-to-head bis-benzimidazoles to discriminate between the 136 possible tetranucleotide sequences may be further enhanced by flanking sequence preferences. These remain to be systematically explored.

Biolocical Activity

Some of these bis-benzimidazoles have been examined for potential cytotoxic effects.

A preliminary study tested compounds 8, 9 and 13 against a group of ovarian carcinoma cell lines. Table 1 shows that all compounds are cytotoxic at the $\mu$M level, with activity significantly greater than that shown by Hoechst 33258. The dimethylamino derivative (13) is over 10-fold more active than the others in three out of the four lines. It is noteworthy, that the compound (13) also shows significant activity in several ovarian lines in the NCI 60-cell line panel. The compound with least in vivo activity, the hydrophobic dimethoxy derivative (8), has been examined in an in vitro tumour model with the ADJ/PC6 plasmacytoma, where, it showed 44% tumour inhibition with ip administration.

TABLE 1

Cytotoxicity ($IC_{50}$ values in $\mu M$) of bis-benzimidazole compounds, for 96 hour exposure in a panel of four ovarian cell lines

| COMPOUND | A2780 | A2780-PT$^R$ | CH1 | SKOV-3 |
|---|---|---|---|---|
| 8 | 13.5 | 5.1 | 3.8 | 16.5 |
| 9 | 4.3 | 2.7 | 1.05 | 16 |
| 13 | 0.235 | 0.115 | 0.24 | 0.375 |
| Hoechst 33258 | 12.0 | 9.5 | 26.5 | >100 |

Compounds 8 and 13 were then tested more extensively against a range of carcinoma cell lines: MCF-7 (breast,); RKO and H630 (colon); A2780 and OAW42 (ovary) and H838 (lung).

TABLE 2

$IC_{50}$ values ($\mu M$) following 96 hour exposure to the compound.

| Cell line | Compound 8 | Compound 13 |
|---|---|---|
| MCF-7 | 0.177, 0.172 | 0.043, 0.069 |
| RKO | 0.613, 0.184, 0.645, 0.645 | 0.187, 0.106, 0.256, 0.158 |
| H630 | 0.183, 0.187, >1 $\mu M$, 0.232 | 0.049, 0.174, 0.28, 0.167 |
| A2780 | 0.136, 0.135, >1 $\mu M$, >1 $\mu M$ | 0.176, 0.132, 0.653, 0.103 |
| OAW42 | 0.167, 0.617, 0.175 | 0.14, 0.138, 0.06 |
| H838 | >1 $\mu M$, 0.275 | 0.16, 0.077 |

Figures in bold were determined using cell counting method, all other values by the MTT assay. The results show that both compounds have potent activity against a wide range of tumour cells, with compound 13 of consistently greater activity than compound 8.

The growth inhibition assays reported above were carried out using standard techniques, some examples of which are detailed below.

Growth Inhibition

Assessment of growth inhibition was performed in a small panel of (e.g.) human ovarian carcinoma cell lines using the Sulforhodamine B (SRB assay) (Kelland et al, Cancer Research 54, 5618–5622 (1994). The cell lines grew as monolayers in Dulbecco's Modified Eagle's medium containing 10% foetal bovine serum (Imperial Laboratories, Andover, UK) supplemented with 2 mM glutamine and 0.5 $\mu$g/ml hydrocortisone in 6% $CO_2$/94% air. The compound to be tested was dissolved in 10% dimethylsulfoxide. Cells were seeded into 96-well microtitre plates at 3000–5000 per well and allowed to attach overnight. Serial dilutions of drug in growth medium were then added to quadruplicate wells (with 8 control untreated wells) and left to incubate under normal growth conditions for 96 hr, unless otherwise stated. The medium was then removed and wells fixed with 10% trichloroacetic acid and stained with 0.4% SRB in 1% acetic acid as described previously (Kelland et al ref). Basic amino acid content in each well was then measured by solubilizing the bound SRB with 10 mM Tris and using a Titertek Multiscan MCC/340 MKII plate reader set at 540 nm. Mean absorbance was then expressed as a percentage of the control untreated well absorbance and plotted vs drug concentration. Comparisons were made in terms of $IC_{50}$ values, (the concentration that reduced the mean absorbance to 50% of those in control wells) and Resistance Factors (RF, the $IC_{50}$ in a resistant subline vs its parent line).

Hollow Fibre Assay

The hollow fibre assay was used for the initial in vivo evaluation of the compounds (M. G. Hollingshead et al, Life Sciences 57, 131–141 (1995). The CH1 ovarian cell line, for example, was prepared by trypsinization and seeded at $1 \times 10^7$ single cells/ml into 2 cm polyvinylidene fluoride (PVDF) fibres (Spectrum, Laguna Hills, Calif.) and heat-sealed. Three days later, following incubation of fibres in growth medium, fibres were implanted into the peritoneal cavity (ip) of nude mice using a trochar. One day later (day 4 after seeding into fibres), mice were treated with either a single maximum tolerated dose of a test compound (4 mg/kg, ip administration) or vehicle (10% DMSO/90% arachis oil). Six days later, fibres were removed and the number of viable cells assessed in treated versus control fibres using the calorimetric MTT assay and measuring absorbance at 540 nm (Mosmann: J. Immunol Methods, 65, 55–63 (1983).

Human Tumour Xenograft

Tumour fragments from the CH1 human ovarian xenograft (corresponding to the CH1 cell line) were implanted subcutaneously into the flanks of adult female nude mice. Animals bearing established tumours (largest diameter of 6–8mm) were then randomized (day 0) into treatment groups of 6 mice to receive either a test compound (at the predetermined maximum tolerated dose of 4 mg/kg) or vehicle (10% MDSO/90% arachis oil). Animals were dosed by intraperitoneal injection on days 0, 4 and 8 following randomization.

Tumour size was determined twice weekly by caliper measurements, and tumour volumes calculated (volume=[a× b²×Π]/6, where a and b are orthogonal tumour diameters. Tumour volumes could then be expressed as a percentage of the volume at the start of treatment (relative tumour volume).

In Vitro Transcription Assay

Compound (13) has been examined in an in vitro transcription assay. It effectively inhibits transcription at a number of A/T sites, consistent with the above data. In addition, compound (13) inhibited transcription at least 10-fold more efficiently than compound (9), consistent with its increased cytoxicity. It is thus tempting to speculate that the activity of (13) in vitro and in vivo may be related to its potent ability to inhibit transcription specifically at a small sub-set of A/T sites. The relatively low affinity of compound (13) for 5'-TATA sites suggests that it is less likely to block TATA-box binding proteins at the start of transcription, by contrast with Hoechst 33258.

What is claimed is:

1. A method of treatment of a neoplastic disease in a patient in need of said treatment by administering a therapeutically effective amount of a compound of the formula:

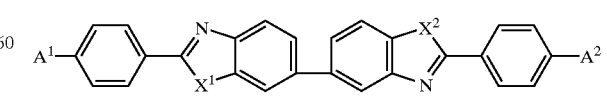

where $X^1$ and $X^2$ are each independently selected from NH, O and S and $A^1$ and $A^2$ are independently selected from: —Y—Q—Z where Y is selected from O, NH and S; Q is selected from —$(CH_2)_n$— where n is 0–10 and carbocyclic 3–7 membered rings; and Z is selected from H, $NR^3R^4$ (where each of $R^3$ and $R^4$ is selected from H; a saturated or unsaturated carbon chain of up to 10 carbon atoms or a ring of up to 7 carbon atoms), or a heterocyclic ring; and —LM where M is an alkylating agent functionality selected from nitrogen mustard functionalities, and L is a linking group; or a pharmaceutically acceptable salt thereof.

2. A method according to claim 1 wherein $X^1$ and $X^2$ are the same.

3. A method according to claim 1 wherein $A^1$ and $A^2$ are the same.

4. A method according to claim 1 wherein at least one of $X^1$ and $X^2$ is NH.

5. A method according to claim 1 wherein at least one of $A^1$ and $A^2$ contains as group Z a heterocyclic ring of 3–8 atoms including 1–3 heteroatoms selected from O, S and N.

6. A method according to claim 1 wherein at least one of $A^1$ and $A^2$ contains as group Z a group —LM where M is an alkylating agent functionality selected from nitrogen mustard functionalities.

7. A method according to claim 6 wherein in said group —LM L is a group —$O.C(O).(CH_3)_3$—.

8. A method according to claim 1 wherein $X^1$ and $X^2$ are NH and $A^1=A^2$=OR where R is H or $C_{1-10}$ alkyl.

9. A method according to claim 8 wherein R is H or Me.

10. A method according to claim 1 wherein $X1$ and $X^2$ are NH and $A^1=A^2$=O.C(O)—$(CH_2)_3$—[1,4-phenyl]—N$[(CH_2)_2Cl]_2$.

11. A method according to claim 1 wherein $X^1$ and $X^2$ are NH and $A^1=A^2$=—O.$(CH_2)_3$—$NMe_2$.

12. A method according to claim 6 wherein M is —$N(CH_2CH_2Cl)_2$.

* * * * *